(12) United States Patent
Agarwal

(10) Patent No.: US 12,161,459 B1
(45) Date of Patent: Dec. 10, 2024

(54) SYSTEM AND METHODS FOR CORRECT NAVIGATION OF AN INSTRUMENT INSIDE A HUMAN BODY

(71) Applicant: Anumana, Inc., Cambridge, MA (US)

(72) Inventor: Animesh Agarwal, San Francisco, CA (US)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/641,254

(22) Filed: Apr. 19, 2024

(51) Int. Cl.
| | |
|---|---|
| A61B 5/06 | (2006.01) |
| A61B 5/00 | (2006.01) |
| A61B 18/00 | (2006.01) |
| A61B 18/14 | (2006.01) |

(52) U.S. Cl.
CPC .............. *A61B 5/068* (2013.01); *A61B 5/062* (2013.01); *A61B 5/7267* (2013.01); *A61B 2018/00351* (2013.01); *A61B 2018/00577* (2013.01); *A61B 18/1492* (2013.01); *A61B 2562/0223* (2013.01)

(58) Field of Classification Search
CPC ......... A61B 5/062; A61B 5/068; A61B 34/20; A61B 2034/2051
See application file for complete search history.

(56) References Cited

U.S. PATENT DOCUMENTS

| | | | | |
|---|---|---|---|---|
| 2011/0158488 | A1* | 6/2011 | Cohen | A61B 6/527 382/128 |
| 2012/0265054 | A1* | 10/2012 | Olson | A61B 34/20 600/424 |
| 2013/0066193 | A1* | 3/2013 | Olson | A61B 5/062 600/424 |
| 2020/0138330 | A1* | 5/2020 | Thompson | A61B 5/6833 |
| 2023/0321446 | A1 | 10/2023 | Rowland et al. | |

FOREIGN PATENT DOCUMENTS

| | | |
|---|---|---|
| JP | 2022545355 A | 10/2022 |
| WO | 1998049938 A1 | 11/1998 |
| WO | 2020212916 A1 | 10/2020 |

OTHER PUBLICATIONS

E Monteiro et al; Convolutional Neural Network for non-invasive magnetic foreign body localization in the human body; 11th Brazilian Congress on Metrology (Metrologia 2021) Journal of Physics: Conference Series 2606 (2023).

* cited by examiner

*Primary Examiner* — Carolyn A Pehlke
(74) *Attorney, Agent, or Firm* — Caldwell Intellectual Property Law

(57) ABSTRACT

A system for correct navigation of an instrument inside a human body, comprising a reference instrument disposed at a first region of an anatomical part, a roving instrument disposed at a second region of the anatomical part, and a control circuit coupled with the reference instrument and the roving instrument, configured to receive a plurality of magnetic locations and a plurality of first impedance locations from the reference instrument, generate a localization model as a function of the plurality of magnetic locations and the plurality of first impedance locations, receive a second impedance location from the roving instrument, and generate an updated second impedance location of the roving instrument, using the localization model, as a function of the second impedance location.

18 Claims, 8 Drawing Sheets

SYSTEM AND METHODS FOR CORRECT NAVIGATION OF AN INSTRUMENT INSIDE A HUMAN BODY

FIELD OF THE INVENTION

The present invention generally relates to the field of medical device positioning systems. In particular, the present invention is directed to a system and methods for correct navigation of an instrument inside a human body.

BACKGROUND

With advancement in healthcare technology, various mapping systems are being used to track medical devices, such as catheters, while they are inside a human body. Existing technology may use an impedance-based tracking system, or a magnet-based tracking system in order to track the position of the catheter. However, there are various challenges in the existing mapping system, for example, spatial requirements, human errors, and interferences due to human anatomy. The various challenges in the existing mapping system may impact accuracy and clinical decision-making.

SUMMARY OF THE DISCLOSURE

In an aspect, a system for correct navigation of an instrument inside a human body is described. The system includes a reference instrument disposed at a first region of an anatomical part, wherein the reference instrument includes at least one magnetic sensor and a first impedance sensor. The system also includes a roving instrument disposed at a second region of the anatomical part, wherein the roving instrument includes a second impedance sensor. The system further includes a control circuit communicatively connected to the reference instrument and the roving instrument, wherein the control circuit includes at least a processor and a memory communicatively connected to the at least a processor, wherein the memory contains instructions configuring the at least a processor to receive a plurality of magnetic locations and a plurality of first impedance locations from the reference instrument, generate a localization model as a function of the plurality of magnetic locations and the plurality of first impedance locations, receive a second impedance location from the roving instrument, and generate an updated second impedance location of the roving instrument, using the localization model, as a function of the second impedance location.

In another aspect, a method for correct navigation of an instrument inside a human body is illustrated. The method includes receiving, by a control circuit, a plurality of magnetic locations and a plurality of first impedance locations from a reference instrument disposed at a first region of an anatomical part, wherein the reference instrument includes at least one magnetic sensor and a first impedance sensor, generating, by the control circuit, a localization model as a function of the plurality of magnetic locations and the plurality of first impedance locations, receiving, by the control circuit, a second impedance location from a roving instrument disposed at a second region of the anatomical part, wherein the roving instrument includes a second impedance sensor, and generating, by the control circuit, an updated second impedance location of the roving instrument, using the localization model, as a function of the second impedance location.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for correct navigation of an instrument inside a human body. In an embodiment, system as described in the present disclosure may utilize a combination of impedance and magnetic sensors to accurately determine the position of instruments within a patient's body.

Aspects of the present disclosure can be used to improve real-time tracking of medical devices within complex anatomical parts. Aspects of the present disclosure can also be used to dynamically adjust the operation of these devices based on continuous impedance and location feedback. This is so, at least in part, because system may implement a localization model with real-time data integration and processing capabilities, allowing for immediate adjustments in instrument locations.

Aspects of the present disclosure allow for implantation of one or more machine learning algorithms to predict and adjust the trajectory of medical instruments. Exemplary embodiments illustrating aspects of the present disclosure are described below in the context of several specific examples.

Figure 1:
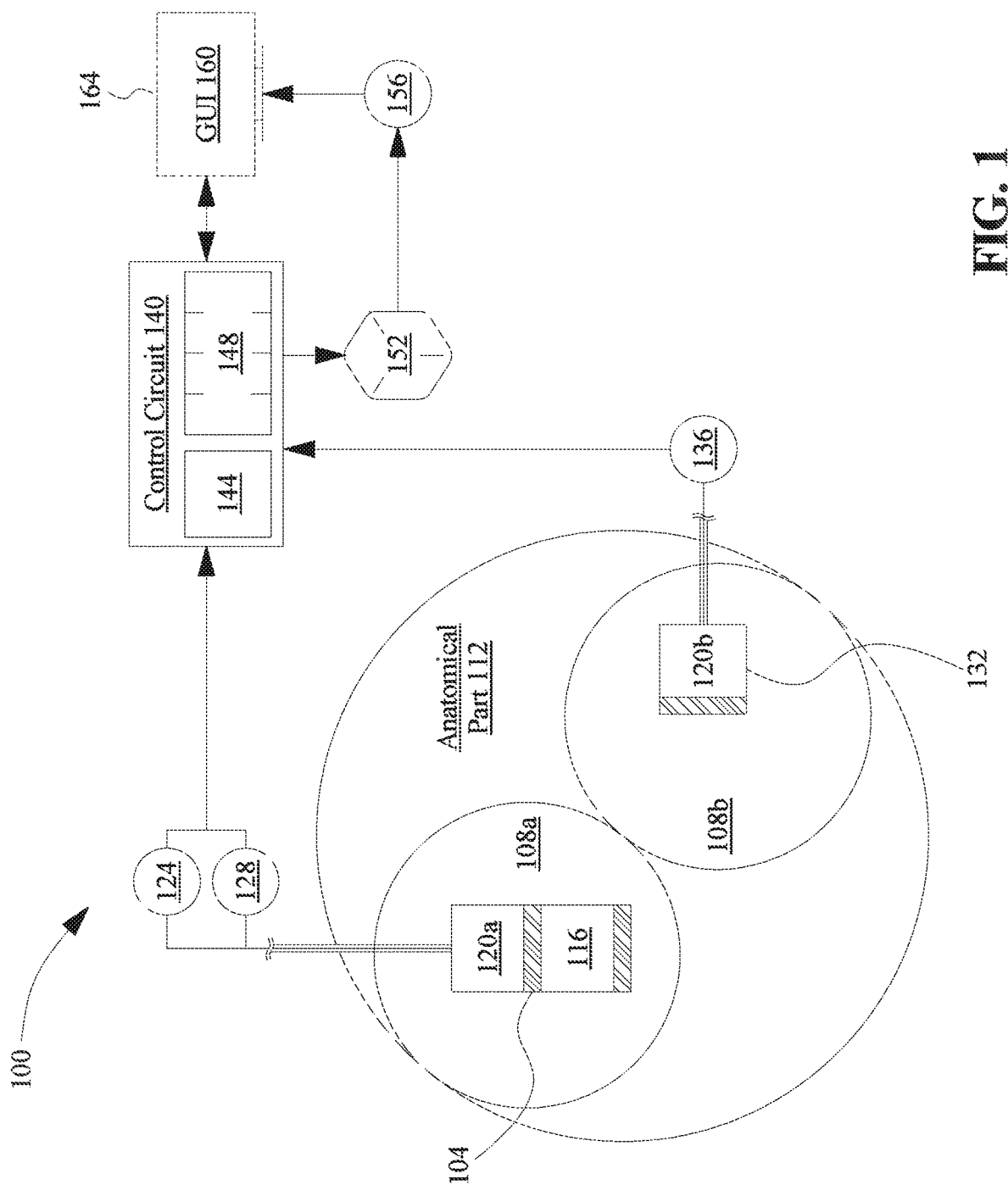
FIG. 1 illustrates a schematic diagram of an exemplary embodiment of a system for correct navigation of an instrument inside a human body.

Referring now to FIG. 1, an exemplary embodiment of a system 100 for correct navigation of an instrument inside a human body is illustrated. As used in this disclosure, an "instrument" is any device or tool that can be navigated within a human body for diagnostic, therapeutic, or otherwise exploratory purposes. Exemplary instruments may include, without limitation, catheters, endoscopes, probes, introducers, sheaths, needles, and any other surgical tools designed for minimally invasive procedures. Instruments may be used for various medical procedures including, without limitation, diagnostic imaging to targeted therapy, biopsy collection, among others. Instruments and system 100 as described herein may be operated by a user, such as, without limitation, a healthcare provider, a clinician, a technician and the like. In some cases, user may utilize a location of an instrument such as reference instrument and roving instrument as described below, inside an organ of a patient's body for visualization or navigation purposes.

With continued reference to FIG. 1, in some cases, instruments may be misplaced or inaccurately positioned due to the complex and variable nature of human anatomy. In some cases, mislocution of instruments may lead to adverse consequences, including without limitation, procedural complications, increased risk of injury to surrounding tissues, prolonged operation times, need for additional corrective procedures, and the like. As a non-limiting example, in cardiac ablation therapy, inaccurate positioning of a catheter may result in ineffective treatment or damage to health cardiac tissue, potentially leading to arrhythmias or other cardiac dysfunctions. The present disclosure discloses system 100 and method of use to correct and prevent inaccurate positioning of instruments within human body, thereby minimizing the risk of procedural complications and enhance efficacy of treatments that contributes to the overall safety and comfort of patients during medical procedures.

With continued reference to FIG. 1, system 100 includes a reference instrument 104 disposed at a first region 108*a* of an anatomical part 112. As used in this disclosure, a "reference instrument" is an instrument designed to establish a baseline or reference point for navigation and localization within the human body. In one embodiment, reference instrument 104 may be used to calibrate system 100 and provide initial data e.g., data describing plurality of magnetic locations and plurality of first impedance locations, necessary for accurate navigation of other instruments such as roving instrument as described in further detail below. In some cases, reference instrument 104 may be configured to reference instruments 104 may be continuously or periodically transmit data signal regarding its positions and electrical characteristics of surrounding tissues. In some embodiments, user may select a specific area, i.e., a "first region" of anatomical part 112 within patient's body as a starting point (or benchmark for subsequent procedure), for example, an easily identifiable landmark within patient's body such as, without limitation, entrance of blood vessel, beginning of a gastrointestinal tract, or any other area of anatomical part 112 known for its distinct electrical or structural properties.

With continued reference to FIG. 1, as used in this disclosure, an "anatomical part" is any organ, tissue, or specific area within human body that is the target of a medical procedure or investigation. In some cases, anatomical part 112 may include, without limitation, heart, lungs, blood vessels, gastrointestinal tract, brain, musculoskeletal structures, among others. It should be noted that the choice of first region 108*a* within anatomical part 112 may be determined based on subsequent procedure's objectives, characteristics of anatomical part 112, and/or the need for navigation and positioning of medical instruments to achieve desirable outcomes. As a non-limiting example, in context of treating atrial fibrillation (i.e., a type of heart disease characterized by irregular and often rapid heart rate), anatomical part 112 of interest may include patient's heart, and more specifically the left atrium. In some cases, first region 108*a*, in this case, may be chosen as pulmonary vein ostia where the pulmonary veins connect to left atrium.

With continued reference to FIG. 1, in one or more embodiments, reference instrument 104 may include a plurality of sensors. As used in this disclosure, a "sensor" is a device or a module capable of detecting, measuring, and/or transmitting information about a particular physical property or condition. In some cases, plurality of sensors may include a group of devices that may be configured to detect one or more inputs and/or phenomenon and transmit information related to such detection. In some embodiments, plurality of sensors may include medical sensors designed for providing real-time data that inform the positioning, movement, and operation of one or more instruments as described herein. Exemplary sensor may include, without limitation, magnetic sensors, impedance sensors, temperature sensors, pressure sensors, optical sensors, ultrasonic sensors, and the like. As a person skilled in the art, upon reviewing the entirety of this disclosure, will be ware of various type of sensor may be employed, as well as specific type of data that each type of sensor acquires, that are essential to understanding the environment in which the instrument is operating and to properly adjusting its navigation as described in further detail below.

With continued reference to FIG. 1, as a non-limiting example, reference instrument 104 includes at least one magnetic sensor 116 and a first impedance sensor 120*a*. A "magnetic sensor," for the purpose of this disclosure, is a device that measures magnetic fields or magnetic disturbances. In some embodiments, at least one magnetic sensor 116 may be configured to detect reference instrument's 104 position and orientation relative to a generated magnetic field around patient body or anatomical part 112. In some cases, at least one magnetic sensor 116 may offer a non-invasive means to track, in environments where optical visibility is limited, such as within the internal structures of human body, reference instrument's 104 path and positioning accurately. In one embodiment, at least one magnetic sensor 116 may be configured to measure a magnetic location. As described herein, a "magnetic location" is a specific set of spatial coordinates or position information derived from an interaction of magnetic sensor with an external magnetic field. As a non-limiting example, magnetic location may include an exact position and orientation of reference instrument 104 within a three0dimensional space e.g., patient's body or anatomical part 112. In some cases, at least one magnetic sensor 116 may be configured to measure a plurality of magnetic locations, as the magnetic location may vary as the instrument moves within magnetic field.

With continued reference to FIG. 1, an "impedance sensor," as described herein, is a device designed to measure the electrical impedance of the tissues through which it passes or comes into contact. Electrical impedance is the measure of the opposition that a circuit presents to a current when a voltage is applied. In some cases, impedance sensor may detect data describing types of tissues surrounding instrument, based on their electrical properties. As a non-limiting example, different tissues, such as blood, muscle, fat, and bone may have distinct electrical impedance characteristics due to their composition and structure. Impedance sensor may be configured to differentiate between types of tissues by measuring impedance levels, thereby identifying an instrument location in relation to specific anatomical structures and detecting changes in tissue type as the instrument moves. For instance, in a cardiac procedure such as catheter ablation for treating arrhythmias, impedance sensor may provide one or more impedance measurements that help ensure an instrument, such as an ablation catheter is in proper contact with heart tissue before energy is delivered. In some cases, first impedance sensor 120a may be configured to measure a first impedance location. As used in this disclosure, an "impedance location" is a specific set of data or measurements that reflect the electrical impedance characteristics of tissues at a specific location within patient's body. In one or more embodiments, impedance location may be obtained by measuring a resistance and reactance encountered by an electrical current as it passes through anatomical part 112 which varies depending on the type and condition of anatomical part 112.

Figure 2:
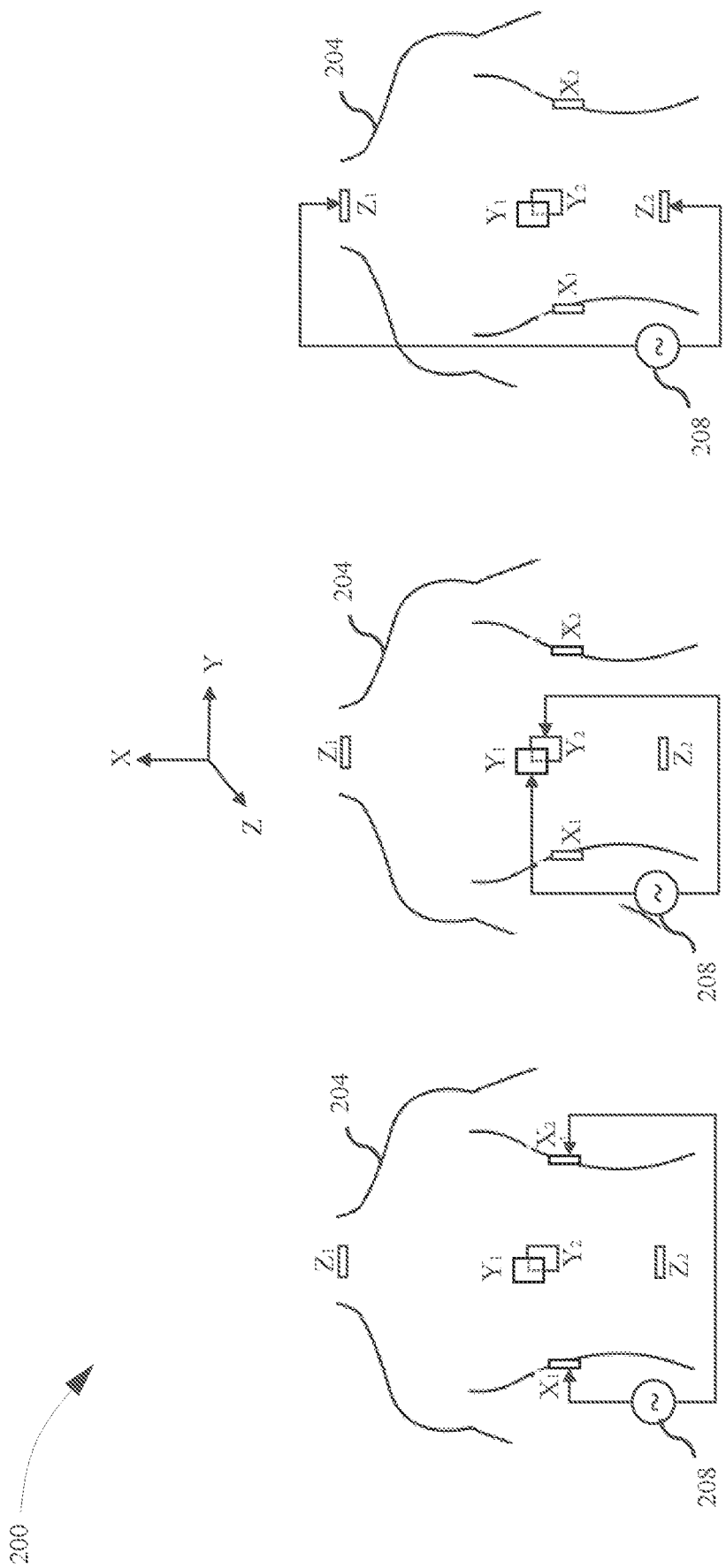
FIGS. 2A-C illustrate exemplary diagrams for implementation of an impedance sensor.

With continued reference to FIG. 1, in one embodiment, reference instrument 104 may include a first sensing array containing at least one magnetic sensor 116 and a second sensing array containing first impedance sensor 120a. At least one magnetic sensor 116 may include one or more magnetic field detection coils communicatively connected to reference instrument 104, providing a controlled low strength AC magnetic field of patient's body and signals to estimate positions e.g., plurality of magnetic positions 124 in first region 108a of anatomical part 112. In one embodiment, each magnetic location of plurality of magnetic locations 124 may include, without limitation, a three-dimensional (3D) coordinate e.g., ($M_x$, $M_y$, $M_z$), and an orientation associated with the position of reference instrument 104 inside first region 108a of anatomical part 112. first impedance sensor 120a may include one or more pair of surface electrodes (as shown in FIGS. 2A-C), and a plurality of electrodes attached to reference instrument 104. In some cases, one or more pair of surface electrodes, such as patches, may provide a controlled low strength AC voltage in first region 108a of anatomical part 112, and plurality of electrodes may provide a signal to estimate positions e.g., plurality of first impedance positions 128 in first region 108a of anatomical part 112. In one embodiment, each first impedance location of plurality of first impedance locations 128 may include, without limitation, a 3D coordinate e.g., ($D_x$, $D_y$, $D_z$) associated with the position of the reference instrument 104 inside first region 108a of anatomical part 112.

With continued reference to FIG. 1, system 100 includes a roving instrument 132 disposed at a second region 108b of anatomical part 112. As used in this disclosure, a "roving instrument" is a medical device configured to move or be navigated through regions within human body. Unlike reference instrument 104 as described above, which may serve as a stationary or initial point of calibration for system 100, roving instrument 132, in one or more embodiments, may be characterized by its mobility and its role in directly engaging with one or more target areas within anatomical part 112. As a non-limiting example, roving instrument 132 may include a medical device or a set of medical devices that is capable of traveling within patient's body. Exemplary roving instrument 132 may include, without limitation, catheters, endoscopes, biopsy needles, and/or any other surgical tools. In some cases, roving instrument 132 may be controlled externally by a user e.g., a physician or in other cases, automatically by control circuit of system 100 as described in further detail below. In a non-limiting embodiment, "second region" where roving instrument is disposed includes a specific target area within anatomical part 112 (e.g., any organ, tissue, or specific area within human body) such as heart, brain, vascular system, or gastrointestinal tract where medical procedure is to be performed.

With continued reference to FIG. 1, in some cases, roving instrument 132 may be used to collect electrical activity associated with second region 108a. In an embodiment, reference instrument 104 and roving instrument 132 may be configured to collect electrical activities associated with an organ, in addition to locations of reference instrument 104 and roving instrument 132 in anatomical part 112. Such data may then be presented to one or more medical professionals e.g., clinician in order to accurately visualize the organ and navigate within the patient's body. As a non-limiting example, roving instrument 132 may be used to collect electrical signals generated by heart or brain. In some cases, electrical signal may include, without limitation, electrocardiogram (ECG) signals, electroencephalogram (EEG) signals, electromyography (EMG) signals, and/or the like. For instance, in treatment of atrial fibrillation, system 100 may be configured to collect ECG data containing erratic electrical signal identifying areas for targeted ablation in addition to locations of roving instrument 132 within left atrium.

With continued reference to FIG. 1, in some embodiments, roving instrument 132 includes a second impedance sensor 120b to measure a second impedance location 136 of roving instrument 132. Second impedance sensor 120b may include any impedance sensor as described above. In some cases, second impedance location 136 may provide a live, real-time navigation within patient's body. In one embodiment, roving instrument 132 may include a third sensing array containing second impedance sensor 120b. As a non-limiting example, at least one second impedance sensor may include one or more pair of surface electrodes attached to roving instrument 132. In some cases, one or more pair of surface electrodes, such as patches, may provide a controlled low strength AC voltage in second region 108b of anatomical part 112, and plurality of electrodes may provide a signal to an estimate position e.g., second impedance position 136 for the roving instrument 106 in second region 108b of anatomical part 112. In one embodiment, second impedance location 136 may include, without limitation, a 3D coordinate e.g., (x, y, z), associated with the position of the roving instrument 132 inside second region 108b of anatomical part 112.

With continued reference to FIG. 1, however, impedance location associated with respective instruments as described herein may not be accurate, thereby affecting accuracy of detected impedance location. This may affect clinical decision-making due to incorrect localization and visualization of medical devices. It should be noted that, although at least one magnetic sensor 116 is configured to measure plurality of magnetic locations 124 may provide an accurate location data, the size of at least one magnetic sensor 116 may be large, thereby causing difficulty in navigation due to the spatial arrangement in patient's body. Therefore, at least in part, at least one magnetic sensor 116 may not be employed for smaller parts of a medical instrument. System 100 and method described herein may be implemented to overcome the aforementioned problems associated with localization, visualization, or otherwise navigation of medical instruments inside organ of patient's body by leveraging a machine learning process as described in further detail below.

With continued reference to FIG. 1, system 100 includes a control circuit 140 communicatively connected to reference instrument 104 and roving instrument 132. A "control circuit," for the purpose of this disclosure, is an integrated circuit or a collection of interconnected circuits designed to manage, control, and/or interface with one or more functionalities in a system. Control circuit 140 includes at least a processor 144 communicatively connected to a memory 148. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, in a non-limiting example, control circuit 140 may be configured as a primary platform or base that provides essential infrastructure, resources, and interfaces to facilitate the operation of other connected or integrated components as described herein. Control circuit 140 may include any computing device as described in this disclosure, including without limitation, a microcontroller, microprocessor, digital signal processor (DSP) and/or system on a chip (SoC) that provide one or more services, resources, or data to other computing devices. Control circuit 140 may include, be included in, and/or communicate with a mobile device such as a mobile telephone or smartphone. Control circuit 140 may include a single computing device operating independently, or may include two or more computing device operating in concert, in parallel, sequentially or the like; two or more computing devices may be included together in a single computing device or in two or more computing devices. In some cases, control circuit 140 may include but is not limited to, for example, a computing device or cluster of computing devices in a first location and a second computing device or cluster of computing devices in a second location. In other cases, control circuit 140 may include a main unit or a primary circuit in a network that controls communications and/or provide a central point of interface.

With continued reference to FIG. 1, in some cases, at least a processor 144 may include a multi-core processor, wherein the "multi-core processor" is an integrated circuit that contains at least two cores on a single chip. In some cases, at least two processor cores may work simultaneously, allowing multiple tasks to be executed in parallel. A "core," for the purpose of this disclosure, is an individual processor unit within a larger processing unit (e.g., central processing unit [CPU] or graphics processing unit [GPU]). In some cases, "core" may be used interchangeably with the terminology "processor" in this disclosure. Each core of at least two cores may be capable of reading and/or executing one or more program instructions, performing arithmetic operations, managing data, and/or communicating with other components within system 100. In a non-limiting example, at least a processor 144 may include a dual-core processor, quad-core processor, hexa-core processor, octa-core processor, many-core processor, or any processor that may perform simultaneous multi-threading (SMT) and/or dynamic core allocation. In some cases, at least a processor 144 may include one or more integrated graphics cores. In some cases, at least a processor 144 may include a cache architecture, wherein each core may include a private L1 (and in some cases, L2) cache, and all cores may share a larger L3 cache. In some cases, at least a processor 144 may integrate at least two cores that are not identical, for example, and without limitation, a high-performance "heavy" core may be combined with an energy-efficient "lite" core. Control circuit 140 may choose the best core for a task based on power and/or performance needs.

With continued reference to FIG. 1, in some cases, at least a processor 144 may implement a network-on-chip design. Control circuit 140 may interface or communicate with one or more additional devices as described below in further detail via a network interface device. Network interface device may be utilized for connecting control circuit 140 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device.

With continued reference to FIG. 1, a "memory," for the purpose of this disclosure, is a device used to store programs or data on a temporary or permanent basis for use in control circuit 140 or other computing devices. In some cases, memory 148 may include a space for data to be read or written. In a non-limiting example, memory 148 may include a random access memory (RAM). In some cases, RAM may include a dynamic RAM (DRAM) that stores each bit of data in a separate capacitor within control circuit 140 and being constantly refreshed to maintain the data. In other cases, RAM may include a static RAM (SRAM) that uses one or more flip-flops to store data (i.e., no need for refreshing). In one or more embodiments, memory 148 may be read only (i.e., ROM). Data that is stored in ROM may be hard-wired and cannot be easily altered or re-written. In some cases, memory may retain data even after the power of control circuit 140 is turned off; however, in some cases, data within memory 148 may be wiped and/or removed after control circuit 140 has been turned off and/or use of a particular software has been terminated. In some cases, memory 148 may be programmable. In some cases, user may erase memory 148 (with UV light) and reprogram memory 148. In some cases, memory 148 may include a flash memory e.g., USB drive, memory card, solid-state drive (SSD), or the like. In some cases, memory 148 may include cache memory, wherein at least a processor 144 may store data used most often in the cache memory, thereby making it instantly available to speed up the at least a processor 144. Other exemplary embodiments of memory 148 may include, without limitation, magnetic memory (e.g., hard disk drive [HDD]), optical memory, magnetic tape memory, phase-change memory (PCM), ferroelectric RAM (FeRAM or FRAM), and the like. In some cases, control circuit 140 may include one or more computing devices dedicated to data storage, security, distribution of traffic for load balancing, and the like. In a non-limiting example, memory 148 may include a secondary memory such as an HDD configured to be a long-term storage device in which an operating system and other information is stored. In some cases, data may be retrieved from secondary memory and transmitted to primary memory e.g., RAM during operation of control circuit 140.

With continued reference to FIG. 1, control circuit 140 may distribute one or more computing tasks as described below across a plurality of computing devices of computing device, which may operate in parallel, in series, redundantly, or in any other manner used for distribution of tasks or memory between computing devices. Control circuit 140 may be implemented, as a non-limiting example, using a "shared nothing" architecture. In some cases, control circuit 140 may be designed and/or configured to perform any method, method step, or sequence of method steps in any embodiment described in this disclosure, in any order and with any degree of repetition. For instance, control circuit 140 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Control circuit 140 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, at least a processor 144 is configured to receive a plurality of magnetic locations 124 and a plurality of first impedance locations 128 from reference instrument 104. In one or more embodiments, reference instrument 104 may be configured to transmit one or more data streams containing both spatial (magnetic) and electrical (impedance) characteristics of first region 108*a* within anatomical part 112 to at least a processor 144. In some cases, plurality of magnetic locations 124 and/or plurality of first impedance locations 128 may include time-series; for example, and without limitation, each magnetic location of plurality of magnetic locations 124 and/or each first impedance location of plurality of first impedance locations 128 may be associated with a timestamp, and these locations may be ordered in time order based on the associated timestamps. As a non-limiting example, at least a processor 144 may be configured to track a spatial trajectory and positioning of reference instrument 104 within first region 108*a* of anatomical part 112.

With continued reference to FIG. 1, in some cases, receiving plurality of magnetic locations 124 and plurality of first impedance locations 128 may include periodically moving reference instrument 104 within first region 108*a* of anatomical part 112. In some cases, at least a processor 144 may be configured to orchestrate the movement of reference instrument 104 in a manner that optimizes data collection process (e.g., comprehensive coverage and high-resolution mapping of first region 108*a*); for instance, and without limitation, control circuit 140 may instruct reference instrument 104 to move in a predetermined pattern, such as a spiral, linear, back and forth, or grid pattern within first region 108*a* to systematically gather plurality of magnetic locations 124 and plurality of first impedance locations 128 across the entirety of first region 108*a*. In some cases, at least a processor 144 may be configured to maintain a maximum displacement, minimum displacement, and/or displacement range from roving instrument 132 while moving reference instrument 104. Processor may be configured to compare derived displacement between reference instrument and roving instrument with one or more of a maximum displacement, a minimum displacement, and/or a displacement range and condition operations on this comparison. Processor may be configured to compare derived displacement between reference instrument and roving instrument with one or more of a maximum displacement, a minimum displacement, and/or a displacement range and condition operations on this comparison. For instance, processor 144 may be configured only to collect data where roving instrument 132 and reference instrument 104 have a displacement from one another within a certain range. Such constraint may ensure that reference instrument 104 remains within a certain range from roving instrument 132, thereby optimizing the relevance and accuracy of collected data for guiding roving instrument. In some cases, maximum displacement, minimum displacement, and/or displacement range may be set based on factors such as, without limitation, the size of anatomical part 112, nature of the procedure, technical capabilities of instruments, and/or the like.

With continued reference to FIG. 1, as a non-limiting example, as reference instrument 104 moves within first region 108*a*, plurality of magnetic locations 124 and plurality of first impedance locations 128 may be collected from multiple locations. System 100 as described herein may adapt any changes within anatomical part 112 that may occur during the procedure, such as movements caused by patient's breathing or shifts in tissue properties, by periodically update locations and impedance data. As a non-limiting example, as patient's anatomical environment changes (whether due to natural movements e.g., breathing, or due to alterations in tissue properties during procedure), at least one processor 144 may update plurality of magnetic locations 124 and plurality of first impedance locations 128 to reflect the new conditions. Such dynamic update of reference data (i.e., plurality of magnetic locations 124 and plurality of first impedance locations 128) may enable system 100 to refine further processing steps or operations of system components e.g., localization model as described below in real-time. In other cases, regular movement, and data collection by reference instrument 104 may be used to verify the stability and accuracy of system 100 itself; for instance, and without limitation, any drift or error in system 100 may be detected and corrected accordingly. As a non-limiting example, if reference instrument 104 is moved along a known path within a predefined area of left atrium but system 100 calculate a deviation from this path based on received magnetic and first impedance locations, at least a processor 144 may signal a potential drift or error. Upon detecting such a discrepancy, a recalibration process as described in further detail below may be initiated.

With continued reference to FIG. 1, in other cases, plurality of magnetic locations 124 and plurality of first impedance locations 128 may include historical locations gather from previous procedures. As a non-limiting example, receiving plurality of magnetic locations 124 and plurality of first impedance locations 128 may include retrieving pre-existing locations stored in a database, wherein the at least a processor 144 is in communication with and has the access to the database. In some cases, database may include a remote database. In one or more embodiments, Database may be implemented, without limitation, as a relational database, a key-value retrieval database such as a NOSQL database, or any other format or structure for use as database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described above. Data entries in database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in database may store, retrieve, organize, and/or reflect data and/or records.

With continued reference to FIG. 1, at least a processor 144 is configured to generate a localization model 152 as a function of plurality of magnetic locations 124 and plurality of first impedance locations 128. As used in this disclosure, a "localization model" is a computational or mathematical framework designed to predict or determine a position of a medical instrument within human body based on input data. localization model 152, in some cases, may function by executing a machine learning process. A "machine-learning process," as used in this disclosure, is a process that automatedly uses a body of data known as "training data" and/or a "training set" (described further below in this disclosure) to generate an algorithm that will be performed by at least a processor 144 to produce outputs given data provided as inputs; this is in contrast to a non-machine learning software program where the commands to be executed are determined in advance by a user and written in a programming language. A machine-learning process may utilize supervised, unsupervised, lazy-learning processes and/or neural networks, described further below. As a non-limiting example, generating localization model 152 may include training one or more machine learning models using one or more machine learning algorithms as described below.

With continued reference to FIG. 1, in some embodiments, reference instrument 104 may use at least one magnetic sensor 116 to determine one or more precise spatial positions (i.e., plurality of magnetic locations 124) within anatomical part 112 such as a heart in patient's body, while first impedance sensor 120a may measures one or more sets of electrical properties of cardiac tissue at one or more measurement sites (i.e., plurality of first impedance locations 128) simultaneously. In some cases, magnetic locations may serve as ground truth location (a reliable, precise measurement of reference instrument's 104 spatial position within patient's body) and on the other hand, first impedance locations serve as corresponding input variables. In one embodiment, generating localization model 152 may include creating a training dataset by correlating plurality of first impedance locations 128 (as inputs) and plurality of magnetic locations 124 (as outputs). Localization model 152 may then be trained using created training dataset via supervised learning.

With continued reference to FIG. 1, as a non-limiting example, generating localization model 152 may include training a neural network to minimize a loss function based on a difference (or a relationship) between each magnetic location of plurality of magnetic locations 124 and each first impedance location of plurality of first impedance locations 128. Trained neural network may accurately correlate physical position (i.e., magnetic location) with physiological data (i.e., impedance locations), thus, at least in part, learning to predict a given instrument's location within human body with desired precision. Loss function may quantify discrepancy or error between predicted locations derived from plurality of first impedance locations 128 and plurality of magnetic locations 124 as determined by reference instrument 104. In some cases, by minimizing the loss, localization model 152 such as neural network may adjust model parameters to improve its predictions. In some cases, localization model 152 may include a transfer function generated based on the minimized loss function, wherein the "transfer function" is a mathematical representation that defines the relationship between input and output of the model. In one embodiment, transfer function may encapsulate how the model translate, for example, impedance measurement (input) into spatial locations (output) based on the correlation formed during the training process as described above.

With continued reference to FIG. 1, in some cases, transfer function may be derived from localization model's 152 architecture, including, without limitation, model's weights and biases, which may be optimized during training process to minimize determined loss function. As a non-limiting example, generated transfer function may essentially model the relationships between one or more electrical properties of anatomical part 112 (as captured by first impedance sensors 120a) and their corresponding physical locations within anatomical part 112 (as determined by at least one magnetic sensors 116). At least a processor 144 may apply transfer function to new impedance measurements, such as, without limitation, second impedance location 136 to predict a corresponding spatial location with a higher degree of accuracy in real-time, even in the absence of direct magnetic locations. Determination of loss function and generation of transfer function are described in further detail below with reference to FIG. 3.

With continued reference to FIG. 1, in one or more embodiments, localization model 152 may include a calibration mode, wherein control circuit 140 may be configured to calibrate, using at least a processor 144, localization model 152 using known positions within anatomical part 112. In some cases, such calibration may take place prior to a procedure. As a non-limiting example, known positions such as plurality of magnetic locations 124 and/or plurality of first impedance locations 128 may establish a baseline locations within anatomical part 112 that have been verified through imaging or previous procedures. In other cases, localization model 152 may be dynamically adjusted based on updated magnetic locations and first impedance locations in real-time during a procedure. Localization model 152 may be configured to adapt changes within anatomical part 112 that may occur during the procedure, such as, without limitation, movements caused by patient's physiology or alternations in anatomical landscape during procedure itself. In some cases, localization model 152 under calibration mode may utilize continuous feedback from reference instrument 104 and roving instrument 132 to refine model's accuracy as the procedure progress. As a non-limiting example, calibration of localization model 152 may involve regularly assessing whether the model, in particular, the loss function, is obsolete with respect to a currently received locations. This is described in further detail below with reference to FIG. 3

With continued reference to FIG. 1, it should be noted that, localization model 152 as described herein may employ other machine learning algorithms other than neural networks, such as, without limitation, support vector machines (SVM) or decision trees, to determine a relationship between received locations and an actual location of roving instrument 132. As a person skilled in the art, upon reviewing the entirety of this disclosure, will be aware of the potential to select and adapt machine learning algorithms as described herein based on factors, such as, without limitation, complexity of navigation task, nature of data available (e.g., linear vs. nonlinear), desired performance, available computational resources, and/or the like. Each machine learning algorithm may offer different advantages in terms of learning efficiency, prediction accuracy, computational and overhead, thus, the choice of machine learning algorithm may significantly influence the performance of localization model 152 in practical medical applications.

With continued reference to FIG. 1, at least a processor 144 is configured to receive second impedance location 136 from roving instrument 132. In some cases, receiving second impedance location 136 may include retrieving a plurality of second impedance locations from roving instrument 132 continuously in real-time. At least a processor 144 is then configured to generate an updated second impedance location 156 of roving instrument, using localization model 152, as a function of second impedance location 136. As used in this disclosure, an "updated second impedance location" is a refined estimation of roving instrument's position within anatomical part 112. In one embodiment, updated second impedance location 156 may include an updated location derived by integrating and analyzing real-time second impedance locations collected from roving instrument 132 with predictive capabilities of localization model 152 as described above. As a non-limiting example, localization model 152 may be configured to use the incoming impedance data e.g., second impedance location 136 to determine an accurate, refined current position of roving instrument 132 based on leaned patterns and relationships between plurality of magnetic locations 124 and plurality of first impedance locations 128.

With continued reference to FIG. 1, in some cases, generating updated second impedance location 156 of roving instrument 132 may include applying transfer function or another mathematical model to translate second impedance location 136 into an estimate location with a higher level of precision. In some embodiments, system 100 may be configured to dynamically update second impedance location 136 of roving instrument 132 as it moves. In some cases, system 100 may be configured to provide continuous feedback that may be used to guide roving instrument 132 more accurately toward its target (e.g., second region 108b of anatomical part 112) or to adjust its course in response to unknown anatomical variations or obstacles. As a non-limiting example, one or more operations of roving instrument 132 may be adjusted, by at least a processor 144, based on updated second impedance location 156. In some cases, the speed, orientation, or activation of functionalities of roving instrument 132 may be adjusted to ensure that roving instrument 132 may be optimally positioned and operated within patient's body to achieve the desired procedural outcomes with minimal risk.

With continued reference to FIG. 1, additionally, or alternatively, at least a processor 144 may be configured to iteratively retraining localization model 152 as a function of a current magnetic location and updated second impedance location 156. In one embodiment, localization model 152 may be further adapted for refined through an iterative retraining process by incorporating the most current data; for instance, and without limitation, both magnetic locations (ground truth) and the updated second impedance locations 156 (new inputs), which reflect the latest measurements of electrical properties from roving instrument 132. As a non-limiting example, at least a processor 144 may collect latest magnetic locations and updated second impedance locations 156 during a procedure. In some cases, such data may serve as new input output pairs reflecting the current locations of roving instrument 132 within anatomical part 112 that may be subsequently added to the training set for localization model 152. At least a processor 144 may adjust one or more model parameters e.g., weight and basis of localization model 152 by retraining, using the updated training set, localization model 152. In some cases, retraining of localization model 152 may be done through a training process on a smaller scale since at least a processor 144 is focusing on fine-tuning localization model 152 rather than building it from scratch. In some cases, the process of retraining localization model 152 may be subject to one or more validations that checks the performance of the model prior to deploying the updated localization model.

With continued reference to FIG. 1, at least a processor 144 may be configured to visualize updated second impedance location 156 of roving instrument 132 in real-time within a graphical user interface (GUI) 160 at a display device 164 communicatively connected to control circuit 140. In some cases, at least a processor 144 may be configured to transmit updated second impedance location 156 to GUI 160. Transmission of updated second impedance location 156 may include, and without limitation, wired or wireless transmission, direct or indirect transmission, between at least a processor 144 and display device 164, which allows for reception and/or transmittance of data and/or signal(s) therebetween. As used in this disclosure "a graphical user interface" is a means by which a user and a computer system interact through visual representations. For example, through the use of input devices and software. In some cases, at least a processor 144 may be configured to modify GUI 160 as a function of the updated second impedance location 156 by visually presenting the updated second impedance location 156 through modification of GUI 160. Other exemplary user interface that may be used to output updated second impedance location 156 may include, without limitation, command line interface (CLI), menu-driven user interface, touch user interface, voice user interface (VUI), form-based user interface, any combination thereof and the like.

With continued reference to FIG. 1, in some embodiments, a user may interact with GUI 160 using display device 164 communicatively connected to at least a processor 144 or another other computing device having such display device that distinct from the at least a processor 144. As described herein, a "display device" is a device configured to show visual information. In some cases, display device 164 may include a liquid crystal display (LCD), a cathode ray tube (CRT), a plasma display, a light emitting diode (LED) display, and any combinations thereof. In some cases, display device 164 may include, but is not limited to, a smartphone, tablet, laptop, monitor, tablet, and the like. In some cases, display device may include a separate device that includes a transparent screen configured to display computer generated images and/or information. As a non-limiting example, a GUI 160 may include one or more graphical locator and/or cursor facilities allowing a user to interact with graphical models and/or combinations thereof, for instance using a touchscreen, touchpad, mouse, keyboard, and/or other manual data entry device. In some embodiments, GUI 160 may include icons, menus, other visual indicators, or representations (graphics), audio indicators such as primary notation, and display information and related user controls. As a person skilled in the art, upon reviewing the entirety of this disclosure, will be aware of various ways in which GUI 160 and/or elements thereof may be implemented and/or used as described in this disclosure.

With continued reference to FIG. 1, in one or more embodiments, GUI 160 may be implemented as an interactive platform configured to present spatial and physiological data as described herein in an accessible format. As a non-limiting example, at least a processor 144 may be configured to construct a three-dimensional (3D) map of first region 108a and second region 108b of anatomical part 112 to assist in navigation of roving instrument 132. In some cases, 3D map may include a 3D model of anatomical part 112 being navigated. In some cases, at least a processor 144 may display historical path, current position of roving instrument 132, or both to provide context for movements of roving instrument 132 within anatomical part 112 within patient's body; for example, at least a processor 144 may highlight (in color or using other indicators), on the displayed 3D model updated second impedance location 156 and/or a path of roving instrument 132. Additionally, or alternatively, displaying 3D map may include displaying real-time metrics related to procedure, such as, without limitation, depth of insertion, speed of movement, or orientation of roving instrument 132.

Now referring to FIGS. 2A-C, exemplary diagrams 200 for implementation of an impedance sensor are illustrated. Elements of FIGS. 2A-C are explained in conjunction with elements of FIG. 1. In an embodiment, the at least one impedance sensor may include the one or more pair of surface electrodes attached to the patient's body 204. In an example, the one or more pair of surface electrodes may be positioned for example, but not limited to adjacently, linearly, or with respective axis of a coordinate system. As shown in FIGS. 2A, 2B, and 2C, X-axis surface electrodes are indicated as X1, and X2, Y-axis surface electrodes are indicated as Y1, and Y2, and Z-axis surface electrodes are indicated as Z1, and Z2. Additional configurations for voltage application may include configurations where voltage is applied in a diagonal pattern across electrode pairs to enhance the spatial resolution of impedance location measurement, such as from X1 to Y2 or Z1 to X2, and in a start pattern that interests multiple aces to gain a more comprehensive impedance profile across various tissue interfaces.

With continue reference to FIGS. 2A-C, in operation, an AC voltage is pumped around a first pair of surface electrodes using a voltage source 208. As shown in FIG. 2A, the AC voltage is applied across the X-axis surface electrodes indicated as X1, and X2 to measure the potential drop in X direction. In an example, there may be some resistance to the flow of the AC voltage inside the patient's body 202, thereby introducing a voltage drop at the receiving end X2. Such a decrease in voltage may be referred to as attenuation. Such attenuation may be associated with a distance between the location (such as, X2) where we are providing the voltage, and the supply. Such voltage drop may be utilized by the system 100 to estimate the impedance location of the instrument inside the patient's body, by pumping voltage from 2 different directions such as X-direction, Y-direction, and Z-direction. Additionally, or alternatively, voltage may be applied between electrodes on different axes e.g., between X1 and Y2 to explore diagonal impedance pathways.

As shown in FIG. 2A, in a non-limiting an example, an AC voltage (Vm) may be applied across the X-axis surface electrodes X1, and X2. Further, a voltage drop between X1 and X2 may be measured as a difference between a voltage at surface electrode (X1) and a voltage at surface electrode (X2). Additionally, a mixed-axis voltage application may be implemented where voltage (Vm) may be applied diagonally across electrodes from X1 to Y2 or X2 to Z1 for a cross-sectional impedance location measurement.

As shown in FIG. 2B, AC voltage is applied across the Y-axis surface electrodes indicated as Y1, and Y2 to measure the potential drop in Y direction. In an example, the AC voltage (Vm) may be applied across the Y-axis surface electrodes Y1, and Y2. Further a voltage drop between Y1 and Y2 may be measured as a difference between a voltage at surface electrode (Y1) and a voltage at surface electrode (Y2). Such configuration may be complemented by applying voltage in patterns that intersect primary axis, such as from Y1 to Z2 or Y2 to X1 for an orthogonal assessment of impedance location.

As shown in FIG. 2C, the AC voltage is applied across the Z-axis surface electrodes indicated as Z1, and Z2 to measure the potential drop in Z direction. In an example, the AC voltage (Vm) may be applied across the Z-axis surface electrodes Z1, and Z2. Further a voltage drop between Z1 and Z2 may be measured as a difference between a voltage at surface electrode (Z1) and a voltage at surface electrode (Z2). Similarly, additional configurations such as applying voltage from Z1 to X2 or Z2 to Y1 may be explored to provide a 2D perspective on the impedance characteristics.

Figure 3:
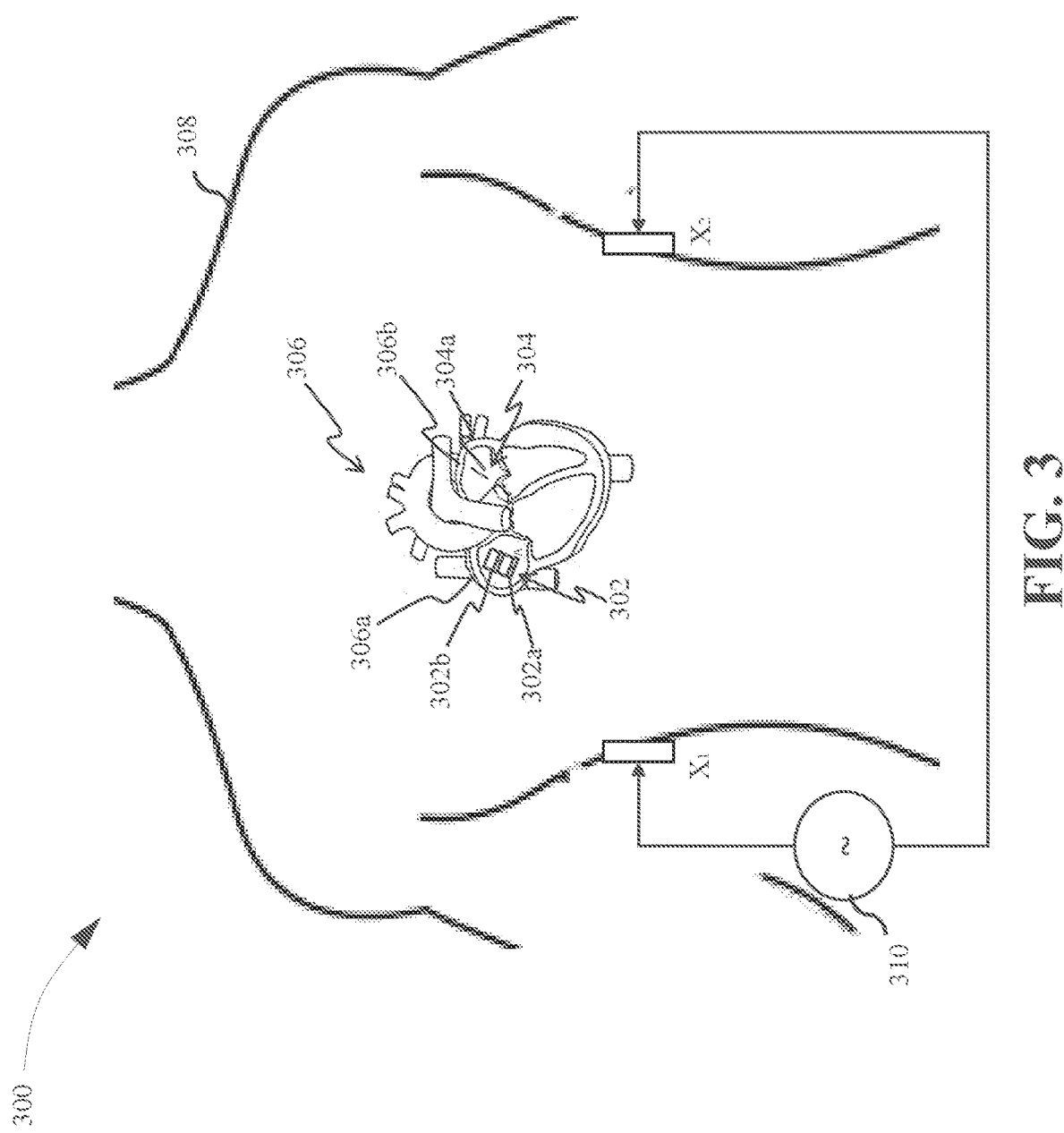
FIG. 3 illustrates an exemplary diagram for implementation of the system.

Now referring to FIG. 3, an exemplary diagram 300 for implementation of the system 100 is illustrated. In one embodiment, in operation, a reference instrument 302 and a roving instrument 304 are inserted into a first region and a second region of an anatomical part, respectively. Since the size of at least one magnetic sensor 302a is larger than impedance sensor, therefore, at least in part, reference instrument 302 may be larger than roving instrument 304 in order to accommodate the spatial requirements for the at least one magnetic sensor 302a. Thus, making roving instrument 304 feasible for more regions of organ of patient's body, such as, without limitation, left atrium of a heart. In some cases, reference instrument 302 is inserted into first region 306a of the anatomical part, such as heart 306 of a patient's body 308, and roving instrument 304 is inserted into second region 306b of heart 306. As a non-limiting example, first region 306a may correspond to a right atrium of heart 306, and second region 306b may correspond to a left atrium of the heart 306.

With continued reference to FIG. 3, in an embodiment, system 100 may be configured to retrieve a plurality of magnetic locations and a plurality of first impedance locations from reference instrument 302 positioned in first region 306a of heart 306. As a non-limiting example, each magnetic location of plurality of magnetic locations may include a 3D coordinate associated with a position of reference instrument 302 inside first region 306a e.g., (Mx, My, Mz), and each impedance location of plurality of impedance locations may include a 3D coordinate associated with a position of reference instrument 302 inside the first region 306a e.g., (Dx, Dy, Dz).

With continued reference to FIG. 3, in an embodiment, system 100 may generate a localization model, such as, without limitation, a neural network by determining a loss function based on plurality of magnetic locations and plurality of first impedance locations. As a non-limiting example, loss function may be calculated using a difference between each coordinate i.e., each magnetic location of plurality of magnetic locations and each first impedance location of plurality of impedance location. For instance, the loss function (E) may be calculated using the following formula:

$$E = \sqrt{[(Mx-Dx)^2 + (My-Dy)^2 + (Mz-Dz)^2]}$$

With continued reference to FIG. 3, in an embodiment, system 100 may be configured to train localization model, such as, without limitation, a neural network to minimize loss function. In some cases, loss function may be minimized based on a difference between each magnetic location of plurality of magnetic locations and each first impedance location of plurality of first impedance locations. As a non-limiting example, localization model may include a convolution neural network (CNN) trained to update a value or a set of values of 3D coordinates such as (Dx, Dy, Dz) associated with plurality of first impedance locations to minimize the loss function. In such an example, system 100 may be configured to estimate an accurate position of reference instrument 302 in first region 306a based on updated first impedance locations and magnetic locations. Further, CNN may be configured to generate a transfer function based on the minimized loss function.

With continued reference to FIG. 3, in an embodiment, 3D coordinates associated with plurality of first impedance locations of at least one first impedance sensor inside first region 306a of heart 306 may be measures as a ratio of potential drop in given direction and potential drop a point A in first region 306a. As a non-limiting example, attenuation corresponding X-coordinate may be measured as a ratio of potential drop in X-direction and potential drop a point A. For instance, the attenuation corresponding to each coordinate (Ax, Ay, Az) may be calculated using the following formula:

$$Ax = \frac{Va - Vx2}{Vx1 - Vx2}, \; Ay = \frac{Va - Vy2}{Vy1 - Vy2}, \; Az = \frac{Va - Vz2}{Vz1 - Vz2}$$

With continued reference to FIG. 3, in an embodiment, the system 102 may be configured to retrieve a second impedance location in real-time from the roving instrument 304 positioned in the second region 306b of the anatomical part. In operation, the magnetic sensor 302a and the first impedance sensor 302b may estimate an accurate position of the reference instrument 302 in the first region 306a based on the magnetic location and the first impedance location. On the contrary, the second impedance sensor 304a may estimate a position of the roving instrument 304 in the second region 306b based on the second impedance location. However, such second impedance location may not be accurate, thereby affecting clinical decision-making due to incorrect visualization and navigation of the roving instrument 304. To overcome the aforementioned problems associated visualization or navigation of the roving instrument 304 in the second region 306b, the present disclosure discloses the system 102 with the neural network. In an embodiment, the system 102 may be configured to generate, using the trained neural network 110, updated second impedance location based on the transfer function and the second impedance location. Therefore, the system 102 may be configured to estimate an accurate position of the roving instrument 304 in the second region 306b based on the updated second impedance location and the transfer function. In example, the trained neural network 110 may generate the updated second impedance location based on the transfer function on the attenuation corresponding to each coordinate (Ax, Ay, Az), thereby determining the accurate second impedance location of the roving instrument 304 in the second region 306b.

With continued reference to FIG. 3, in an embodiment, reference instrument 302 and roving instrument 304 may be simultaneously inserted into first region 306a and second region 306b, respectively. As a non-limiting example, such simultaneous insertion of reference instrument 302 and roving instrument 304 may estimate accurate position of roving instrument 304 in second region 306b in real time, thereby optimizing visualization or navigation of the roving instrument 304 in the second region 306b.

With continued reference to FIG. 3, in some cases, anatomy of patient's body 308 may change; for example, a change in amount of fluid in the body 308, change in electrical properties of tissues, precipitation under the pair of surface electrodes. Such changes may lead to a change in the conductivity of the body 308, thereby altering plurality of first impedance locations measured from reference instrument. In such a case, loss function may vary, resulting in an incorrect determination of the second impedance location for the roving instrument 304. To overcome such problems, system 100 may be configured to receive plurality of magnetic locations and plurality of first impedance locations for reference instrument 302 within first region 306a from reference instrument 302 and one or more second impedance locations for second region 306b from roving instrument 304 continuously in real-time. In an embodiment, system 100 may be configured to dynamically assess whether loss function is obsolete with respect to a currently received locations. As a non-limiting example, system may be configured to re-calibrate, based on assessing loss function is obsolete, another loss function for localization model based on the currently received plurality of magnetic locations and first impedance locations. Thereafter, system 100 may be configured to re-train localization model to minimize the re-calibrated loss function and generate a re-calibrated transfer function. System 100 may be further configured to generate, using re-trained localization model, updated second impedance location for a currently obtained second impedance location.

With continued reference to FIG. 3, a non-limiting example, a loss function may be determined for localization model such as, without limitation, a neural network at a first time period, based on plurality of magnetic locations and first impedance locations for reference instrument 302 within first region 306a. Neural network may be trained to minimize loss function and generate a transfer function, for example, at time t0, a loss function E0 may be determined for reference instrument 302 based on magnetic locations and first impedance locations. Neural network may determine a transfer function H0 based on loss function E0. System 100 may be configured to generate an updated second impedance location based on transfer function H0 and measured second impedance location e.g., a 3D coordinate such as (dx0, dy0, dz0) for roving instrument 304. However, at time t1, there may be changes in the anatomy of patient's body 308, thereby changing first impedance locations from reference instrument 302. As a result, loss function E0 may become obsolete. In such a scenario, another loss function may be re-calibrated for neural network based on currently received magnetic locations and first impedance locations. As a non-limiting example, at time t1 another loss function E1 may be determined for reference instrument 302 based on current magnetic locations and first impedance locations, and a transfer function H1 may be subsequently generated based on newly determined loss function E1. Thereafter, system 100 may be configured to generate updated second impedance location based on generated transfer function H1 and currently obtained second impedance location. Updated second impedance location may include a 3D coordinate e.g., (dx1, dy1, dz1) for roving instrument 304. Such re-calibration of loss function over time may provide an optimum localization, visualization, and navigation of roving instrument 304 inside organ of patient's body.

With continued reference to FIG. 3, in an embodiment, system 100 may be configured to periodically move reference instrument 302 within first region 306a of the heart 306 and determine another loss function for re-training of localization model such as a neural network to solve another loss function to minimize such loss function, based on magnetic locations and first impedance locations received from moved reference instrument 302. System 100 may be configured to maintain a maximum displacement between roving instrument 304 and reference instrument 302 when moving reference instrument 302. For instance, system 100 may be configured only to collect data where roving instrument 304 and reference instrument 302 have a displacement from one another within a certain range. As a non-limiting example, at time t0, magnetic locations and first impedance locations may be received for reference instrument 302 within first region 306a to determine loss function E0 for localization model. However, at time t1, reference instrument 302 may be moved within first region 306a. Therefore, at least in part, updated magnetic locations and first impedance locations may be retrieved for reference instrument 302 within first region 306a to determine another loss function E1 for localization model to re-train the model. Such re-training of localization model over time may provide an optimum localization, visualization, and navigation of roving instrument 304 inside organ of patient's body.

Figure 4:
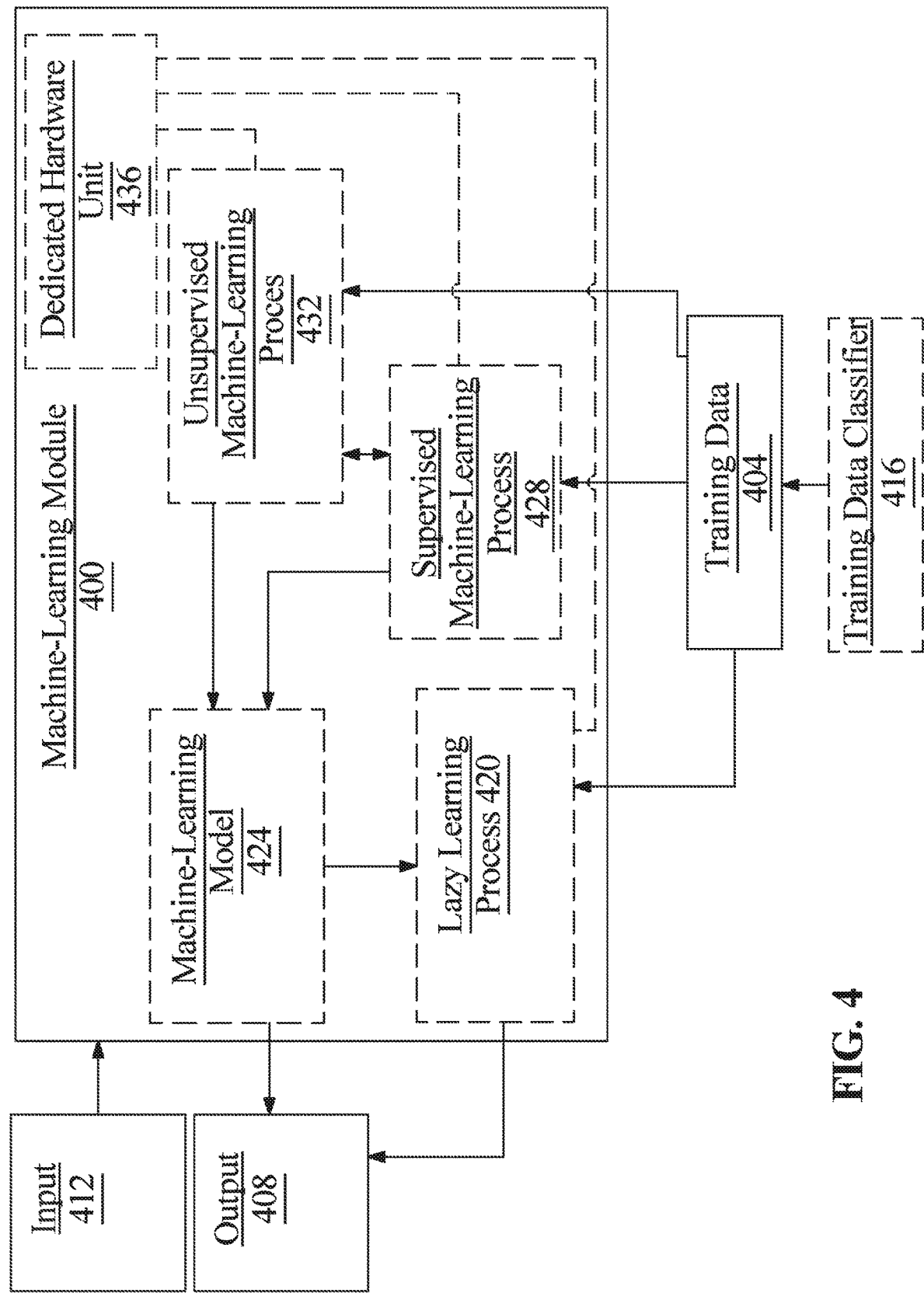
FIG. 4 illustrates a block diagram of an exemplary embodiment of a machine learning module.

Referring now to FIG. 4, an exemplary embodiment of a machine-learning module 400 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 404 to generate an algorithm instantiated in hardware or software logic, data structures, and/or functions that will be performed by a computing device/module to produce outputs 408 given data provided as inputs 412; this is in contrast to a non-machine learning software program where the commands to be executed are determined in advance by a user and written in a programming language.

Still referring to FIG. 4, "training data," as used herein, is data containing correlations that a machine-learning process may use to model relationships between two or more categories of data elements. For instance, and without limitation, training data 404 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 404 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 404 according to various correlations; correlations may indicate causative and/or predictive links between categories of data elements, which may be modeled as relationships such as mathematical relationships by machine-learning processes as described in further detail below. Training data 404 may be formatted and/or organized by categories of data elements, for instance by associating data elements with one or more descriptors corresponding to categories of data elements. As a non-limiting example, training data 404 may include data entered in standardized forms by persons or processes, such that entry of a given data element in a given field in a form may be mapped to one or more descriptors of categories. Elements in training data 404 may be linked to descriptors of categories by tags, tokens, or other data elements; for instance, and without limitation, training data 404 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 4, training data 404 may include one or more elements that are not categorized; that is, training data 404 may not be formatted or contain descriptors for some elements of data. Machine-learning algorithms and/or other processes may sort training data 404 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 404 to be made applicable for two or more distinct machine-learning algorithms as described in further detail below. Training data 404 used by machine-learning module 400 may correlate any input data as described in this disclosure to any output data as described in this disclosure. As a non-limiting illustrative example, exemplary training data may include a plurality of first impedance locations as input correlated with a plurality of magnetic locations as output.

Further referring to FIG. 4, training data may be filtered, sorted, and/or selected using one or more supervised and/or unsupervised machine-learning processes and/or models as described in further detail below; such models may include without limitation a training data classifier 416. Training data classifier 416 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 400 may generate a classifier using a classification algorithm, defined as a processes whereby a computing device and/or any module and/or component operating thereon derives a classifier from training data 404. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 4, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)÷P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 4, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 4, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 4, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 4, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 4, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 4, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 4, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 4, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 4, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 4, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}: X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 4, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 4, machine-learning module 400 may be configured to perform a lazy-learning process 420 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 404. Heuristic may include selecting some number of highest-ranking associations and/or training data 404 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 4, machine-learning processes as described in this disclosure may be used to generate machine-learning models 424. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 424 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 424 may be generated by creating an artificial neural network, such as a convolutional neural network comprising an input layer of nodes, one or more intermediate layers, and an output layer of nodes. Connections between nodes may be created via the process of "training" the network, in which elements from a training data 404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 4, machine-learning algorithms may include at least a supervised machine-learning process 428. At least a supervised machine-learning process 428, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include plurality of first impedance locations as described above as inputs, a plurality of magnetic locations as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 404. Persons skilled in the art, upon reviewing the entirety of this disclosure, will be aware of various possible variations of at least a supervised machine-learning process 428 that may be used to determine relation between inputs and outputs. Supervised machine-learning processes may include classification algorithms as defined above.

With further reference to FIG. 4, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 4, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 4, machine learning processes may include at least an unsupervised machine-learning processes 432. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 432 may not require a response variable; unsupervised processes 432 may be used to find interesting patterns and/or inferences between variables, to determine a degree of correlation between two or more variables, or the like.

Still referring to FIG. 4, machine-learning module 400 may be designed and configured to create a machine-learning model 424 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 4, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 4, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 4, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 4, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 4, one or more processes or algorithms described above may be performed by at least a dedicated hardware unit 436. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 436 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 436 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 436 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 5:
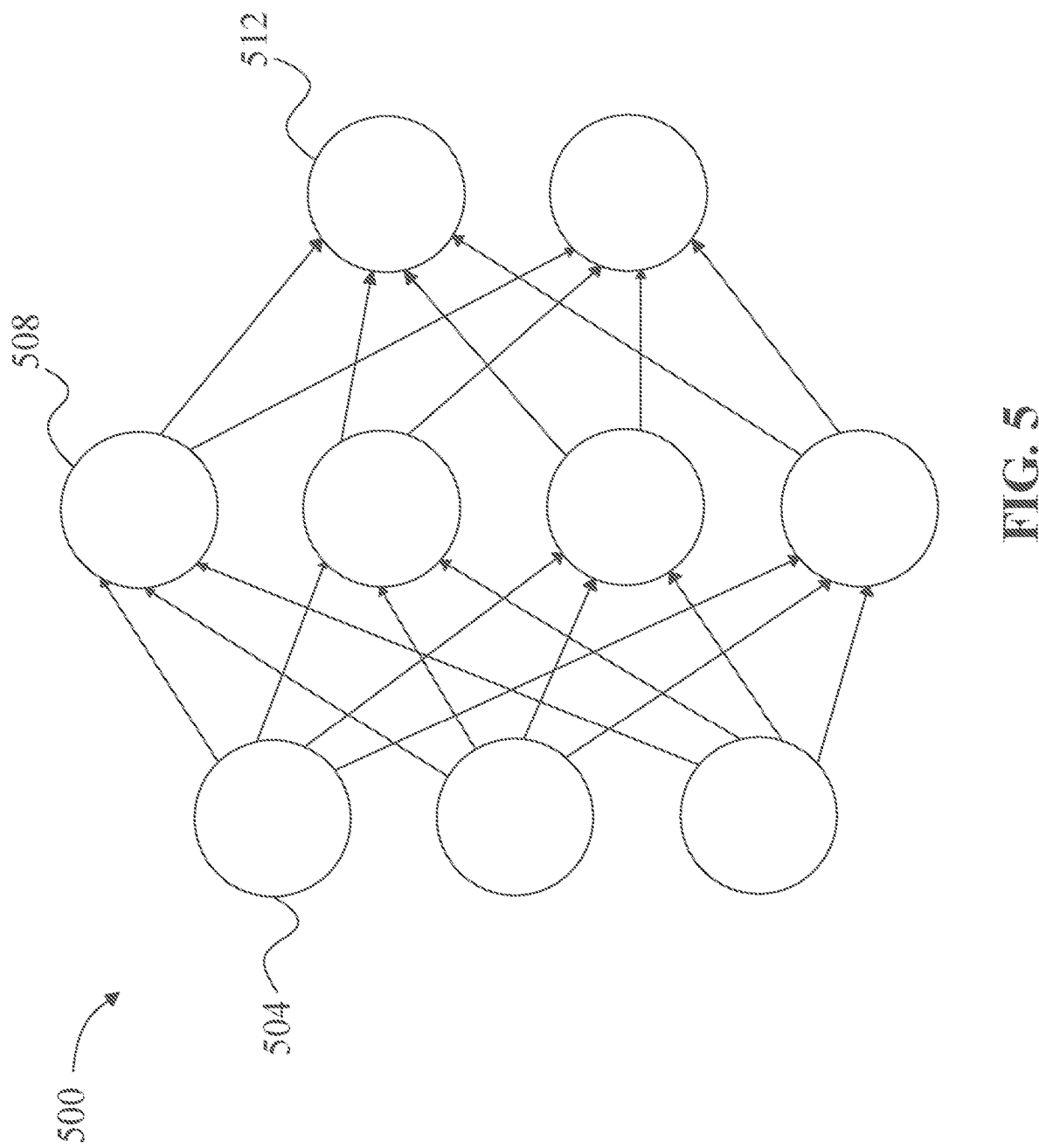
FIG. 5 illustrates a diagram of an exemplary nodal network.

Referring now to FIG. 5, an exemplary embodiment of neural network 500 is illustrated. In some cases, localization model 152 may include a neural network 500. Neural network 500 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 504, one or more intermediate layers 508, and an output layer of nodes 512. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network."

With continued reference to FIG. 5, as a further non-limiting example, a neural network may include a convolutional neural network comprising an input layer of nodes, one or more intermediate layers, and an output layer of nodes. A "convolutional neural network," for the purpose of this disclosure, is a neural network in which at least one hidden layer is a convolutional layer that convolves inputs to that layer with a subset of inputs known as a "kernel," along with one or more additional layers such as pooling layers, fully connected layers, and the like. In some cases, CNN may include, without limitation, a deep neural network (DNN) extension. Mathematical (or convolution) operations performed in the convolutional layer may include convolution of two or more functions, where the kernel may be applied to input data through a sliding window approach. In some cases, convolution operations may enable processor 144 to detect local/global patterns, edges, and any other features described herein within training data. Detected patterns and/or features may be passed through one or more activation functions, such as without limitation, Rectified Linear Unit (ReLU). Additionally, or alternatively, CNN may also include one or more pooling layers, wherein each pooling layer is configured to reduce the dimensionality of input data while preserving essential features within the input data. In a non-limiting example, CNN may include one or more pooling layer configured to reduce the dimensions of feature maps by applying downsampling, such as max-pooling or average pooling, to small, non-overlapping regions of one or more features. CNN may further include one or more fully connected layers configured to combine features extracted by the convolutional and pooling layers as described above. In some cases, one or more fully connected layers may allow for higher-level pattern recognition. In a non-limiting example, one or more fully connected layers may connect every neuron (i.e., node) in its input to every neuron in its output, functioning as a traditional feedforward neural network layer. In some cases, one or more fully connected layers may be used at the end of CNN to perform high-level reasoning and produce the final output such as, without limitation, at least one updated second impedance location. Additionally, or alternatively, each fully connected layer may be followed by one or more dropout layers configured to prevent overfitting, and one or more normalization layers to stabilize the learning process described herein.

Figure 6:
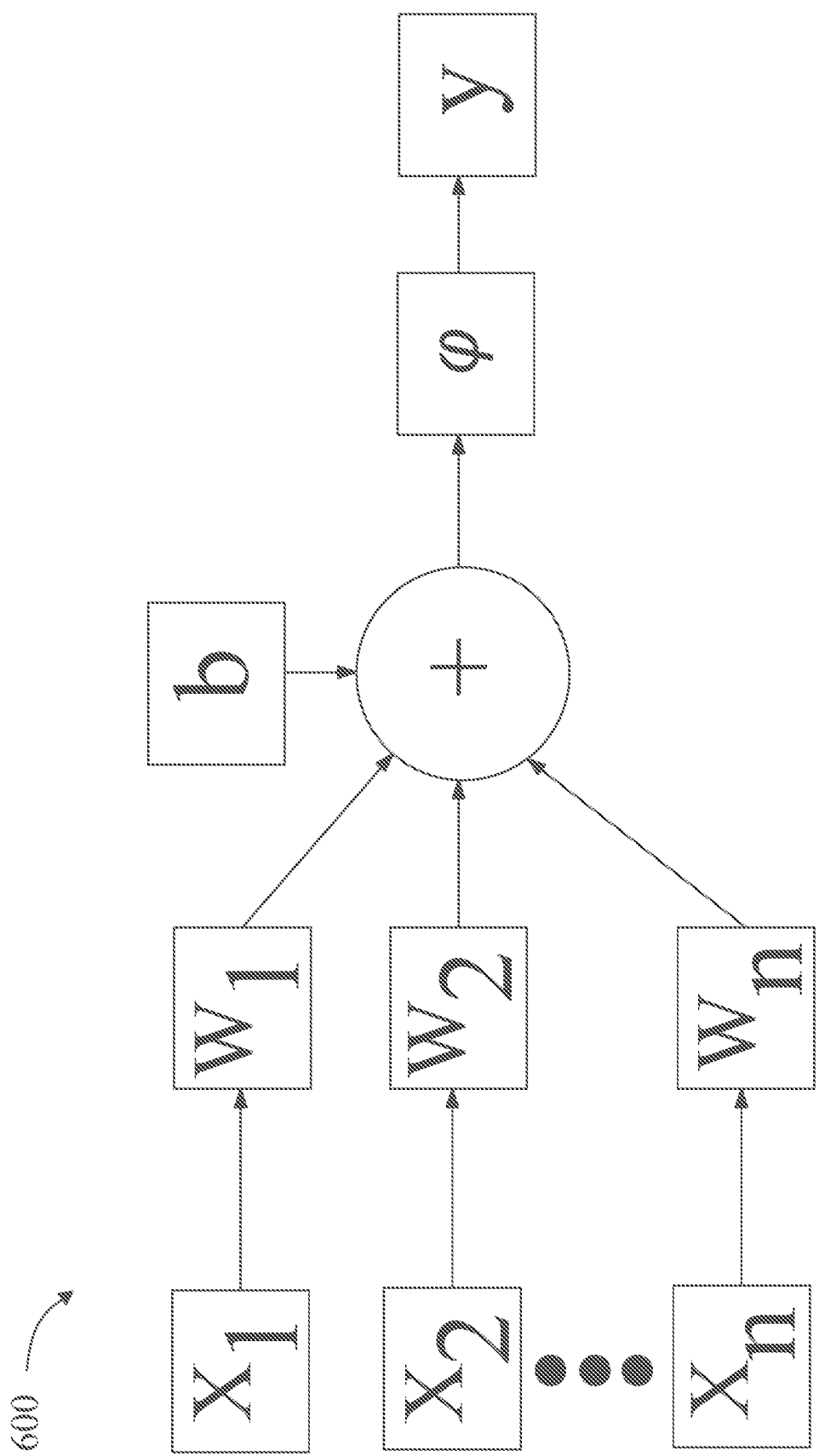
FIG. 6 illustrates a block diagram of an exemplary node.

Referring now to FIG. 6, an exemplary embodiment of a node 600 of a neural network is illustrated. A node may include, without limitation, a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a "leaky" and/or "parametric" rectified linear unit function such as $f(x)=\max(ax, x)$ for some a, an exponential linear units function such as $$f(x) = \begin{cases} x & \text{for } x \geq 0 \\ \alpha(e^x - 1) & \text{for } x < 0 \end{cases}$$

for some value of $\alpha$ (this function may be replaced and/or weighted by its own derivative in some embodiments), a softmax function such as $$f(x_i) = \frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x) = \begin{cases} \alpha(e^x - 1) & \text{for } x < 0 \\ x & \text{for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally, or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 7:
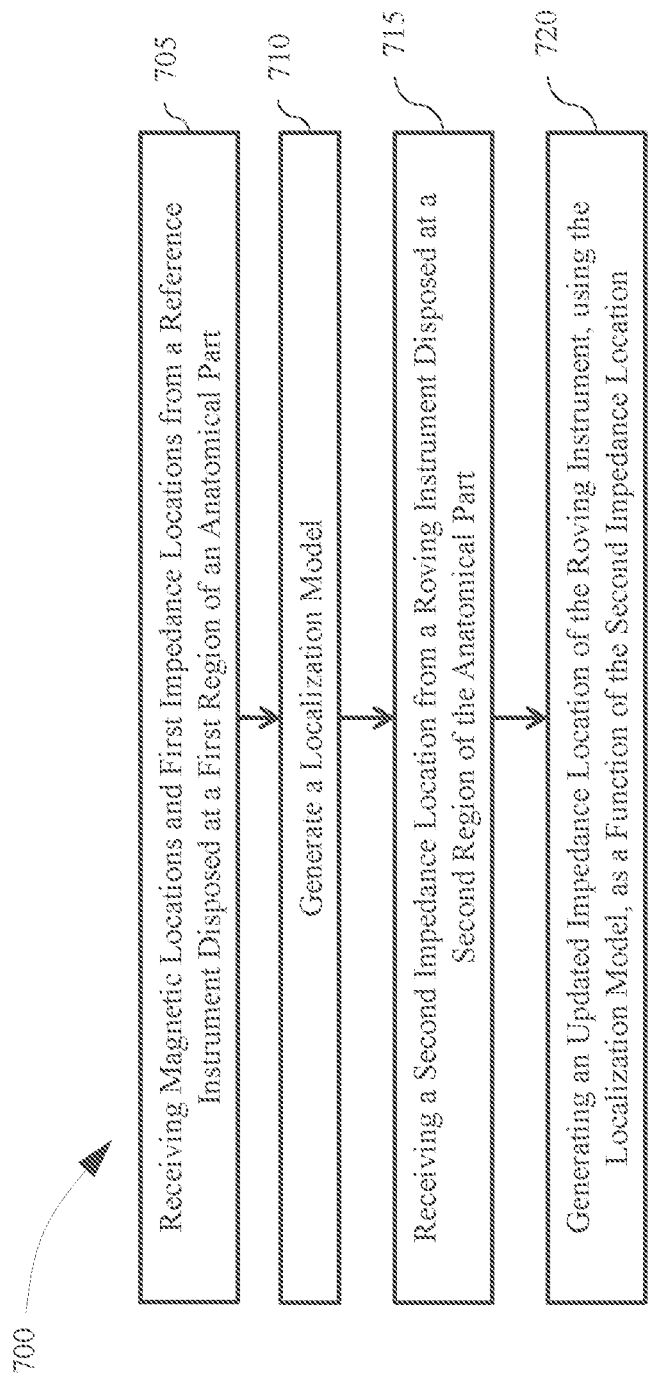
FIG. 7 illustrates a flow diagram of an exemplary embodiment of a method for correct navigation of an instrument inside a human body.

Now referring to FIG. 7, a flow diagram of an exemplary embodiment of a method 700 for correct navigation of an instrument inside a human body is illustrated. Method 700 includes a step 705 of receiving, by a control circuit, a plurality of magnetic locations and a plurality of first impedance locations from a reference instrument disposed at a first region of an anatomical part, wherein the reference instrument includes at least one magnetic sensor and a first impedance sensor. In some embodiments, receiving the plurality of magnetic locations and the plurality of first impedance locations may include periodically moving the reference instrument within the first region of the anatomical part. Method 700 includes a step 710 of generating, by the control circuit, a localization model as a function of the plurality of magnetic locations and the plurality of first impedance locations. Method 700 includes a step 715 of receiving, by the control circuit, a second impedance location from a roving instrument disposed at a second region of the anatomical part, wherein the roving instrument includes a second impedance sensor. Method 700 includes a step 720 of generating, by the control circuit, an updated second impedance location of the roving instrument, using the localization model, as a function of the second impedance location. This may be implemented, without limitation, as described above with reference to FIGS. 1-6.

With continued reference to FIG. 7, in some embodiments, moving the reference instrument may include maintaining, by the control circuit, a maximum displacement between the roving instrument and the reference instrument when moving the reference instrument. In some embodiments, reference instrument and the roving instrument may be simultaneously inserted into the first region and the second region of the anatomical part, respectively. In some embodiments, reference instrument and the roving instrument may be simultaneously inserted into the first region and the second region of the anatomical part, respectively. In some embodiments, generating the localization model may include training a neural network to minimize a loss function based on a difference between each magnetic location of the plurality of magnetic locations and each first impedance location of the plurality of first impedance locations. In some embodiments, the localization model may include a transfer function generated based on the minimized loss function. In some embodiments, receiving the second impedance location may include retrieving a plurality of second impedance locations from the roving instrument continuously in real-time. This may be implemented, without limitation, as described above with reference to FIGS. 1-6

With continued reference to FIG. 7, method 700 may further include a step of iteratively retraining, by the control circuit, the localization model as a function of a current magnetic location and the updated second impedance location. Method 700 may further include a step of visualizing the updated second impedance location of the roving instrument in real-time within a graphical user interface (GUI) at a display device communicatively connected to the control circuit. Method 700 may further include a step of adjusting one or more operations of the roving instrument based on the updated second impedance location. This may be implemented, without limitation, as described above with reference to FIGS. 1-6

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
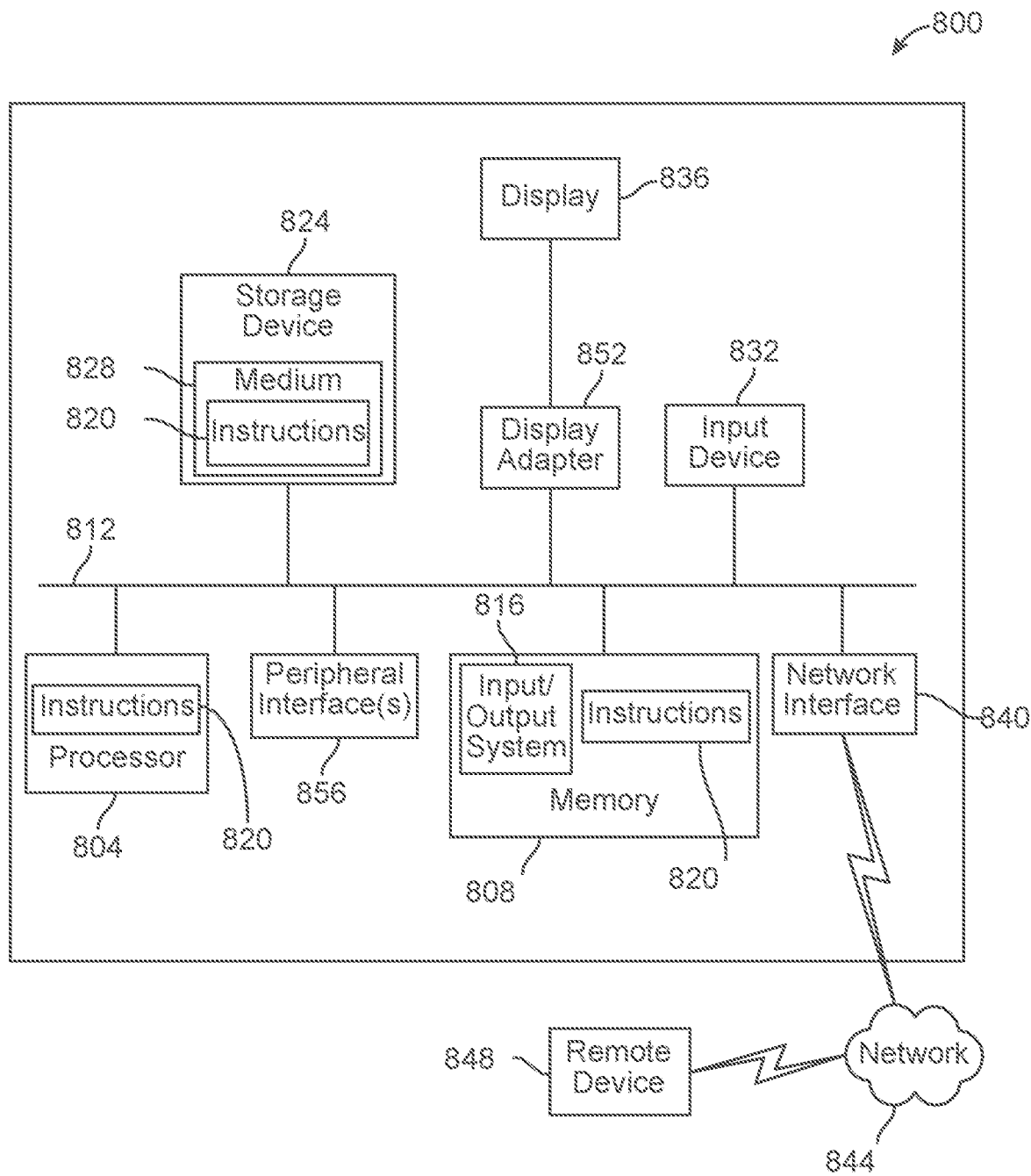
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIRE-WIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for correct navigation of an instrument inside a human body, wherein the system comprises:
   a reference instrument disposed at a first region of an anatomical part, wherein the reference instrument comprises:
   at least one magnetic sensor and a first impedance sensor;
   a roving instrument disposed at a second region of the anatomical part, wherein the roving instrument comprises a second impedance sensor; and
   a control circuit communicatively connected to the reference instrument and the roving instrument, wherein the control circuit comprises:
   at least a processor and a memory communicatively connected to the at least a processor, wherein the memory contains instructions configuring the at least a processor to:
   receive a plurality of magnetic locations and a plurality of first impedance locations from the reference instrument;
   generate a localization model as a function of the plurality of magnetic locations and the plurality of first impedance locations; receive a
   second impedance location from the roving instrument; and
   generate an updated second impedance location of the roving instrument, using the localization model, as a function of the second impedance location;
   wherein receiving the plurality of magnetic locations and the plurality of first impedance locations comprises periodically moving the reference instrument within the first region of the anatomical part.

2. The system of claim 1, wherein the reference instrument and the roving instrument are simultaneously inserted into the first region and the second region of the anatomical part, respectively.

3. The system of claim 1, wherein the memory further contains instructions configuring the at least a processor to: determine a displacement between the roving instrument and the reference instrument, when moving the reference instrument; and compare the displacement with a maximum displacement between the roving instrument and the reference instrument.

4. The system of claim 1, wherein generating the localization model comprises training a neural network to minimize a loss function based on a difference between each magnetic location of the plurality of magnetic locations and each first impedance location of the plurality of first impedance locations.

5. The system of claim 4, wherein the localization model comprises a transfer function generated based on the minimized loss function.

6. The system of claim 1, wherein receiving the second impedance location comprises retrieving a plurality of second impedance locations from the roving instrument continuously and in real-time.

7. The system of claim 1, wherein the memory further contains instructions configuring the at least a processor iteratively retrain the localization model as a function of a current magnetic location and the updated second impedance location.

8. The system of claim 1, wherein the memory further contains instructions configuring the at least a processor to visualize the updated second impedance location of the roving instrument in real-time within a graphical user interface (GUI) at a display device communicatively connected to the control circuit.

9. The system of claim 1, wherein the memory further contains instructions configuring the at least a processor to adjust one or more operations of the roving instrument based on the updated second impedance location.

10. A method for correct navigation of an instrument inside a human body, wherein the method comprises:
    receiving, by a control circuit, a plurality of magnetic locations and a plurality of first impedance locations from a reference instrument disposed at a first region of an anatomical part, wherein the reference instrument comprises:
        at least one magnetic sensor and a first impedance sensor;
    generating, by the control circuit, a localization model as a function of the plurality of magnetic locations and the plurality of first impedance locations;
    receiving, by the control circuit, a second impedance location from a roving instrument disposed at a second region of the anatomical part, wherein the roving instrument comprises a second impedance sensor; and
    generating, by the control circuit, an updated second impedance location of the roving instrument, using the localization model, as a function of the second impedance location;
    wherein receiving the plurality of magnetic locations and the plurality of first impedance locations comprises periodically moving the reference instrument within the first region of the anatomical part.

11. The method of claim 10, wherein the reference instrument and the roving instrument are simultaneously inserted into the first region and the second region of the anatomical part, respectively.

12. The method of claim 10, further comprising: determining, by the control circuit, a displacement between the roving instrument and the reference instrument, when moving the reference instrument; and comparing, by the control circuit, the displacement and a maximum displacement between the roving instrument and the reference instrument.

13. The method of claim 10, wherein generating the localization model comprises training a neural network to minimize a loss function based on a difference between each magnetic location of the plurality of magnetic locations and each first impedance location of the plurality of first impedance locations.

14. The method of claim 13, wherein the localization model comprises a transfer function generated based on the minimized loss function.

15. The method of claim 10, wherein receiving the second impedance location comprises retrieving a plurality of second impedance locations from the roving instrument continuously and in real-time.

16. The method of claim 10, further comprises iteratively retraining, by the control circuit, the localization model as a function of a current magnetic location and the updated second impedance location.

17. The method of claim 10, further comprises visualizing the updated second impedance location of the roving instrument in real-time within a graphical user interface (GUI) at a display device communicatively connected to the control circuit.

18. The method of claim 10, further comprises adjusting one or more operations of the roving instrument based on the updated second impedance location.

* * * * *